(12) United States Patent
Heisig et al.

(10) Patent No.: US 8,969,282 B2
(45) Date of Patent: Mar. 3, 2015

(54) LOW ODOR, HARD SURFACE SPORICIDE

(75) Inventors: Christopher C. Heisig, St. Louis, MO (US); Herbert J. Kaiser, Pontoon Beach, IL (US); Daniel A. Klein, Shiloh, IL (US); Jessica S. Linder, Belleville, IL (US); Katie J. Frey, St. Charles, MO (US); Nancy E. Kaiser, Pontoon Beach, IL (US); Jerry L. Newman, O'Fallon, MO (US)

(73) Assignee: American Sterilizer Company, Mentor, OH (US)

( * ) Notice: Subject to any disclaimer, the term of this patent is extended or adjusted under 35 U.S.C. 154(b) by 944 days.

(21) Appl. No.: 12/322,702

(22) Filed: Feb. 5, 2009

(65) Prior Publication Data

US 2010/0196503 A1 Aug. 5, 2010

(51) Int. Cl.
  *C11D 7/18* (2006.01)
  *A61K 31/327* (2006.01)
  *A01N 59/00* (2006.01)
  *A61K 31/16* (2006.01)
  *A61K 33/40* (2006.01)

(52) U.S. Cl.
  CPC .............. *A61K 31/327* (2013.01); *A01N 59/00* (2013.01); *A61K 31/16* (2013.01); *A61K 33/40* (2013.01)
  USPC ........... 510/375; 510/108; 510/372; 510/382; 510/445; 568/568

(58) Field of Classification Search
  USPC ........... 510/108, 372, 375, 382, 445; 568/568
  See application file for complete search history.

(56) References Cited

U.S. PATENT DOCUMENTS

| | | | |
|---|---|---|---|
| 3,839,234 A | 10/1974 | Roscoe | |
| 4,772,413 A | 9/1988 | Massaux | |
| 4,839,156 A * | 6/1989 | Ng et al. | 424/53 |
| 5,977,053 A * | 11/1999 | Groth et al. | 510/480 |
| 6,238,736 B1 * | 5/2001 | Smith et al. | 427/242 |
| 6,251,845 B1 * | 6/2001 | Herbots et al. | 510/320 |
| 6,530,384 B1 * | 3/2003 | Meyers et al. | 134/25.2 |
| 6,569,281 B2 * | 5/2003 | Brown, Jr. | 156/293 |
| 6,627,590 B1 * | 9/2003 | Sherry et al. | 510/238 |
| 2004/0127381 A1 * | 7/2004 | Scialla et al. | 510/372 |
| 2005/0058719 A1 * | 3/2005 | Ramirez et al. | 424/616 |
| 2006/0019854 A1 * | 1/2006 | Dyer et al. | 510/376 |

FOREIGN PATENT DOCUMENTS

| | | | |
|---|---|---|---|
| EP | 0337576 | * | 10/1989 |
| EP | 0967175 B1 | * | 12/1999 |
| WO | WO 99/57980 | * | 11/1999 |

* cited by examiner

*Primary Examiner* — Ali Soroush
(74) *Attorney, Agent, or Firm* — Hudak, Shunk & Farine Co. LPA (57) ABSTRACT

A low odor, liquid disinfectant composition comprising multiple components, which, upon mixing, provide an aqueous solution comprising low levels of peracetic acid for use in decontaminating articles and surfaces contaminated with bacteria, viruses, fungi and other biological contaminants such as spores, including, but not limited to, *Clostridium difficile* (*C.diff*). The disinfectant composition is prepared just prior to use by combining two or more separately packaged components.

16 Claims, 3 Drawing Sheets

FIG. 1

O.L. = Organic Load
S.B. = Sheep's Blood (Known organic load)
BSA = Bovine Serum albumin (Known organic load)
NGS = Next Generation Sporicide (the inventive compositions)

FIG. 2

PAA = Peracetic Acid

FIG. 3

LOW ODOR, HARD SURFACE SPORICIDE

FIELD OF THE INVENTION

This invention is directed to a low odor, liquid disinfectant composition comprising multiple components, which, upon mixing, provide an aqueous solution comprising low levels of peracetic acid for use in decontaminating articles and surfaces contaminated with bacteria, viruses, fungi, and other biological contaminants, such as spores, including, but not limited to, *Clostridium difficile* (*C.diff*). The disinfectant composition is prepared just prior to use by combining two or more separately packaged components.

BACKGROUND OF THE INVENTION

Hospital-acquired infections linked to exposure to *C.diff* spores are a universal health-care crisis. Infection with *C.diff* is life-threatening to many patient populations, and contamination of equipment, materials, and surfaces with spores produced by *C.diff* bacteria occurs frequently, despite the best efforts at infection control. Part of the reason is that *C.diff* spores can survive on surfaces for long periods and are inherently difficult to destroy. Diligent efforts are necessary to eradicate the spores and require the use of disinfectant cleaning compositions with efficacy against spores and bacteria that produce them.

Similarly, in the pharmaceutical industry, manufacturing facilities have experienced a number of product recalls and plant shutdowns due to contamination with bacteria, viruses, fungi, spores (including spore-forming bacteria) and other biological contaminants. There has been an increase in the use of disinfectant sterilant products for cleaning pharmaceutical manufacturing equipment and surfaces.

The main products used in the cleaning and disinfection of surfaces contaminated with biological materials, specifically spores, are predominately oxidizing compositions, such as liquid or granular hypochlorite solutions (bleach), or hydrogen peroxide-based products such as EAST DEACON™ developed by Sandia National Laboratories. Specific to *C.diff*, the standard practice in most health care institutions is to use a product based upon sodium hypochlorite, also known as bleach. Hypochlorite-based disinfectants have been used with some success for surface disinfection in those patient-care areas where surveillance and epidemiology indicate ongoing transmission of *C.diff*. At present, there are no EPA-registered products with specific claims for inactivating *C.diff* spores, but there are a number of registered products that contain hypochlorite. As discussed below, while achieving efficacy in eradication of spores, use of currently available "bleach" products has many drawbacks.

Products used in the pharmaceutical manufacturing industry to eradicate spores and spore-forming bacteria rely on oxidizing chemistries, one of which is hydrogen peroxide. Like the use of hypochlorite-based products in health care institutions, the use of hydrogen peroxide chemistries for bacterial eradication in the pharmaceutical industry also suffers from many disadvantages.

Many sporicide products are available commercially. In addition to hypochlorite and hydrogen peroxide, products containing alcohols, peracetic acid (PAA), peracetic acid in combination with alcohols, hypochlorite or peroxide, and various products that utilize peroxygen sources and acetyl donors to generate both peracetic acid and hydrogen peroxide, are available as disinfectants or sterilants. These commercially available products have some disadvantages. Generally, alcohol-based disinfectants alone are not effective against *C.diff* or other spores, or spore-forming bacteria. In addition, many of these products have aesthetic and handling disadvantages, such as harshness (acidity or alkalinity), strong odor, and skin and mucous membrane irritation, due to high concentrations of active components. Most currently available products require overly cumbersome personal protective equipment to be used during their application to limit exposure, thus adding to their costs. The use, storage and transportation of these known, decontamination products thus present significant physical and health hazards and logistical challenges in shipping, handling and storage.

Hypochlorite bleach, although efficacious against *C. diff*, is not without these same disadvantages. Sodium hypochlorite has poor materials compatibility. Most sodium hypochlorite products are alkaline in nature and are corrosive to many materials, such as stainless steel, brass and copper. In addition, it has been shown that sodium hypochlorite can "strip away" waxes commonly used on hospital surfaces, making it an impractical choice for mopping applications. Further, sodium hypochlorite is associated with a difficult-to-rinse residue, which may contribute to its "stripping" effect. Finally, sodium hypochlorite demonstrates only moderate efficacy against certain organisms. It degrades rapidly in the presence of an organic soil load, thus negatively impacting its efficacy.

Oxidizing chemistries, such as bleach and hydrogen peroxide formulations, are known to be harsh chemistries requiring specific handling requirements. Depending on concentration, hydrogen peroxide may be subject to stringent handling restrictions. It may also be associated with strong odors and inhalation irritation issues. The OSHA permissible exposure limit (PEL) is 1 ppm for hydrogen peroxide. Some combination products, containing hydrogen peroxide as one component, may still be subject to air shipment restrictions based upon the concentration of hydrogen peroxide. In most cases, the products need to be shipped either by ground or sea causing delays in their arrival at required locations. Air shipment is possible for hydrogen peroxide, but quantities are severely limited and require special packaging.

Both sodium hypochlorite and hydrogen peroxide in high concentrations are corrosive, require special packaging, have limited transportation modalities and unstable without controlled transportation systems. Storage is also problematic. The storage of large amounts of highly corrosive and heat sensitive liquids is a safety issue. Bleach (hypochlorite) decomposes quickly at high temperatures resulting in a significant loss of efficacy and, therefore, has limited shelf life. Hydrogen peroxide spontaneously and irreversibly decomposes at elevated temperatures. Both hypochlorite- and hydrogen peroxide-based materials will also decompose rapidly when subjected to environmental contaminants such as dirt or blowing sand.

It is further noted that in addition to metal substrates, bleach and liquid hydrogen peroxide are incompatible with a number of non-metal substrates such as paints, soft metals, rubbers and plastics.

Finally, another disadvantage of most commercially available hydrogen peroxide and peracetic acid systems is that they cannot be sold as sterile. In order to create sterile products, the systems must be capable of being sterilized with gamma-irradiation. Gamma irradiation is commonly used in the pharmaceutical industry to sterilize cleaning compositions. Most commercial peracetic acid and hydrogen peroxide systems are not stable when exposed to gamma-irradiation and cannot be sterilized in this manner, requiring additional sterilization steps, if a sterile product is needed, adding to the costs associated with their use.

Accordingly, in the health care market and the pharmaceutical industry, an effective sporicide with EPA-approved claims against *C.diff* is needed to address the emerging health care and product contamination issues. *C.diff* spores can live on surfaces for years. *C.diff* spores are very difficult to kill. As mentioned above, sporicide products are available, but most have safety, odor, material compatibility and handling issues, among others. Currently, there are no EPA-approved products to address *C.diff* spores. The current practice in most health care institutions is to use a 10% solution of hypochlorite to clean all articles presumed to be contaminated with *C.diff* spores. There is a need, therefore, for a product having lower odor, better materials compatibility, improved safety profile, less stringent shipping requirements, and less onerous handling and storage parameters than currently existing products.

Formulations comprising peracetic acid, or components capable of generating peracetic acid (PAA) in situ, are effective sporicides and are nearly equivalent to acidified bleach, an industry standard for efficacy. A new sporicide system for each of the above-discussed markets (health care and pharmaceutical manufacturing) has been developed, having unexpected efficacy against spores and spore forming bacteria, such as *C.diff*, as well as other bacteria, virus, or fungi, but without the disadvantages of currently available products. Different embodiments of these inventive systems may be used depending on the needs of the market served; however, the foundation of the chemistry is the same: generation of peracetic acid through the perhydrolysis of tetraacetylethylene-diamine (TAED) using a specifically formulated hydrogen peroxide solution.

Product formulations containing peracetic and/or components for generating peracetic acid are known in the art. For example, systems comprising dry components exist that utilize solid peroxygen sources and acetyl donors, which, when mixed with water, produce peracetic acid (PAA). See e.g., U.S. Pat. No. 5,350,563, directed to a two-part perborate/acetyl donor powdered formulation. While dry product forms have application in certain cases, they are generally limited by slow generation of PAA at room temperature, and, therefore, there is a preference for more rapid acting liquid products in certain applications. Use of dry peroxygen components is disadvantageous due to the time needed to generate hydrogen peroxide before activation (combination) with the acetyl donor. A particular disadvantage to multi-component dry systems is that the components dissolve very slowly in water, such that the desired concentration of active ingredients is not fully available until later stages. There is also an additional risk that undissolved components will remain and not be rinsed away. On the other hand, a system or formulation utilizing a liquid hydrogen peroxide component has been found to generate PAA much faster as the perhydroxyl ion is available immediately upon combination with an acetyl donor, regardless of whether the acetyl donor is in solid or liquid form.

Other liquid commercial products containing both peracetic acid and hydrogen peroxide are also known. For example, a liquid product produced by Decon Labs, known as "SPORGON" comprises 7.35% hydrogen peroxide and 0.23% peracetic acid; however, the high level of hydrogen peroxide in use requires a limitation of exposure. OSHA limits personal hydrogen peroxide exposure to 1 ppm. In addition, the product requires at least three hours to achieve sterilization. Another example is OXONIA ACTIVE, an acidic liquid sanitizer, produced by Ecolab. This product is highly corrosive and has a hydrogen peroxide level of 27.5% and peracetic acid level of 5.8%. The high level of hydrogen peroxide requires, in addition to exposure limits, stringent shipping and handling requirements. In most instances, these products cannot be gamma-irradiated, the preferred method for sterilization of pharmaceutical industry disinfectants.

Liquid systems for generating PAA are also known. By way of example, U.S. Pat. Nos. 6,514,509 and 7,235,252 are directed to systems for preparing organic peroxy acids using a parent solution and activator and requiring a hydroalcoholic environment (at least 10% alcohol) with an acid pH. The alcohol purportedly acts as an additional germicide. In contrast, the present invention does not utilize or require a hydroalcoholic environment and does not utilize strong inorganic acids to maintain an acid pH. Importantly, peracetic acid is generated in an alkaline environment, not acidic, and the resulting product rapidly converts to a neutral pH upon peracetic acid generation. There is no need for an additional germicide.

European Patent 0 598 170 B1 is a cleaning composition based on hydrogen peroxide (or a peroxygen source) combined with acetyl triethyl citrate as a bleach activator. The bleach activator requires emulsification with at least two surfactants having different HLB values. The components are all combined in one unitary liquid composition.

The present invention is based upon combining an acetyl donor, alkalinity agents and a liquid hydrogen peroxide source to produce an effective concentration of peracetic acid in situ to destroy *C.diff* spores. The present invention is a ready-to-use system upon activation (combination of ingredients) and requires no further dilution or manipulation of components. Generation of peracetic acid is much faster due to the immediate availability of the perhydroxyl ion, as compared to products using a dry peroxygen source. Surprisingly, the present formulations are effective at much lower concentrations of peracetic acid than currently available products.

The present invention provides sporicidal formulations having a pH in the neutral range (4-8), which allows for easier disposal versus highly alkaline or acidic products, and has superior materials compatibility against soft metals, plastics, resins and other materials, as compared to bleach. The inventive formulations also result in low odor products that are less caustic or irritating to personnel than existing products, including those containing higher levels of peracetic acid, and may eliminate the need for respiratory protection required for application of higher concentrations of PAA and acidified bleach. They have no detectable levels of acetic acid or hydrogen peroxide. Most commercially available PAA-containing products require the use of acetic acid to stabilize the peracetic acid for longer shelf life, greatly increasing the odor profile. Since peracetic acid is generated in situ with the present invention, there is no need for the addition of acetic acid or any other acid, thus reducing or eliminating the odor profile.

Unexpectedly, the formulations of the present invention are efficacious against a wide range of bacteria, viruses, fungi and spores, including *C.diff*, without the addition of additional biocides or germicides and, hence, are less costly. Microbial efficacy has been shown even in the presence of an organic soil load and at a lower concentration of peracetic acid. Surfactants utilized in the present system are excellent cleaners, improving efficacy in the presence of an organic soil. Finally, the inventive formulations comprise low levels of hydrogen peroxide, which is not subject to stringent shipping and handling requirements.

Tetraacetylethylenediamine (TAED) is the preferred acetyl donor for the present invention. A formulated solution of hydrogen peroxide is the chosen perhydroxyl source. Both TAED and hydrogen peroxide are currently registered EPA-active ingredients. While several different embodiments exist for the inventive formulations, they all share the advantageous properties of preparation at a neutral pH, low odor, better materials compatibility, improved safety profile and high efficacy.

The present invention contemplates two different embodiments: one, a two-part system consisting of a dry TAED powder activator and a liquid formulated hydrogen peroxide solution, and the other, a three-part system consisting of a 2-component liquid TAED activator (comprising a TAED suspension and an alkaline liquid solution) and the same liquid formulated hydrogen peroxide as used in the two-part system. Both systems, upon activation (combination), generate lower levels of peracetic acid with unexpected microbial efficacy.

It is an object of this invention to provide a low odor disinfectant having efficacy against bacteria, viruses, fungi and other biological materials, including spores and spore-forming bacteria, such as C. diff.

It is a further object of this invention to provide a low-odor peracetic acid solution with greatly improved safety and handling features over currently available products.

Still a further object of this invention is to provide a system for rapid generation of peracetic acid in an alkaline pH environment, which quickly drops into the neutral range upon peracetic acid generation, resulting in a product that is usable within a short period of time after combination and having a use life of at least 24 hours.

Yet a further object of this invention is to provide a peracetic acid solution which has efficacy even in the presence of an organic soil load.

It is a further object of this invention to provide an effective, safer alternative to hypochlorite or other oxidizing chemistries for use in health care environments to eradicate C. diff spores.

These and other objects of the invention will be apparent based upon the description herein.

SUMMARY OF THE INVENTION

The invention is directed to a low-odor sporicide based upon the generation of peracetic acid from an acetyl donor combined with liquid hydrogen peroxide. The peracetic acid is generated in an alkaline environment, and the final product has a neutral pH, making it safer and easier to handle and transport. The liquid hydrogen peroxide component allows for rapid generation of peracetic acid compared to conventional products based upon dry peroxygen sources. Surprisingly, the low levels of peracetic acid generated are effective against bacteria, viruses, fungi and other microbes, including spore formers, such as C.diff, without the need for high concentrations of peracetic acid or the addition of other disinfectant or sterilizing agents.

In one embodiment, the inventive composition comprises:
a) a activator blend comprising a solid acetyl donor combined with a solid alkalinity source; and
b) a hydrogen peroxide solution, wherein the acetyl donor and alkalinity source are mixed with the hydrogen peroxide solution just prior to use to form a peracetic acid solution.

In a second embodiment, the inventive composition comprises:
a) a two-part liquid activator comprising in one part, an acetyl donor dispersion, and in the other part, an alkaline solution; and
b) a hydrogen peroxide solution, wherein the acetyl donor dispersion and alkaline solution are mixed with the hydrogen peroxide solution just prior to use to form peracetic acid.

In both embodiments, the hydrogen peroxide solution is the same and comprises hydrogen peroxide in very low amounts, preferably less than 8 weight percent, more preferably less than 3 weight percent, and most preferably less than 1.5 weight percent; a surfactant; fragrance; and water. The lower concentration of hydrogen peroxide avoids shipping and handling restrictions and is safer for use. Once mixed, the hydrogen peroxide content remains close to the original low levels that were present prior to mixing.

The concentration of peracetic acid produced can vary depending on the amounts of activator and hydrogen peroxide solution that are combined.

BRIEF DESCRIPTION OF THE DRAWINGS

The invention will be better understood and other features and advantages will become apparent by reading the detailed description of the invention, taken together with the drawings, wherein.

DETAILED DESCRIPTION OF THE INVENTION

The general chemistry that forms the base of the claimed compositions is peracetic acid, generated from the combination of TAED and hydrogen peroxide at an alkaline pH, as the source of antimicrobial efficacy. Both TAED and hydrogen peroxide are recognized by the EPA as active ingredients. The claimed compositions utilize components that are kept separate until such time as the disinfectant solution is needed. Once mixed, the compositions have a use life of about 24 hours. Typically, the claimed compositions generate from about 0.05 to about 0.25% peracetic acid solutions.

As one component, the inventive compositions comprise an acetyl donor, such as TAED. In the first embodiment, where the activator is in powder or "dry" form, the TAED is first coated with a surfactant or blend of surfactants to aid in dissolution upon activation. The surfactant used to coat the TAED is typically anionic, although the claimed compositions are not limited to anionic surfactants. One useful surfactant is alkyldiphenyl oxide disulfonate, sold as an aqueous 45% active solution under the name DOWFAX C10-L. Other anionic surfactants useful in the present invention include N-oleoyl sarcosinate and dodecylbenzene sulfonic acid.

The surfactant is applied to the TAED as an aqueous solution, wherein the TAED, traditionally water insoluble, is mixed into a slurry. The slurry is then dried, and the resulting "cake" is pulverized into a powder, which is comprised of TAED coated with a surfactant. This "coated" TAED is then blended with two dry alkalinity sources. The complete blend of the "coated" TAED with the dry alkalinity sources comprises the dry "activator" portion of the composition. In this embodiment, the alkalinity sources for the powdered, coated TAED include sodium carbonate and a biodegradable chelating agent such as the tetrasodium salt of iminodisuccinic acid (sold under the trade name BAYPURE CX 100). Advantageously, the iminodisuccinic acid also acts as a chelating agent which aids in the efficacy of the system in the presence of an organic load.

At the time of, or just prior to, use, the dry "activator" is combined with a formulated hydrogen peroxide solution, which contains hydrogen peroxide and a surfactant or blend of surfactants. A formulation of liquid hydrogen peroxide is preferred over a dry perhydroxyl or peroxygen source due to much faster generation of peracetic acid achieved upon combination of the liquid hydrogen peroxide with the TAED activator. When combined (or "activated"), peracetic acid is generated. Depending on the amounts of activator and hydrogen peroxide selected, various concentrations of peracetic acid may be generated. Upon activation, the product, regardless of PAA concentration, will have a 24-hour pot-life (i.e., "shelf" or "use-dilution" life).

In the second embodiment, the "TAED activator" is itself a two-part liquid activator system. As one part of the liquid activator, a TAED dispersion is prepared. TAED is suspended in an aqueous system that includes a suspending agent, and perhaps surfactants and solvents. Typical suspending agents include magnesium aluminum silicate and Xanthan gum. The second part of the liquid activator is an alkaline, aqueous solution comprising an alkalinity source and surfactant(s). The alkalinity source for this embodiment can be a hydroxide, amine or chelating agent, or combinations thereof. Typical examples include sodium hydroxide, monoethanolamine, triethanolamine and 2-amino-2-methyl-1-propanol.

For the two-part liquid TAED activator, anionic or nonionic surfactants may be used. Typical anionic surfactants include N-oleoyl sarcosinate, alkyldiphenyloxide disulfonate, and dodecylbenzene sulfonic acid. A typical nonionic surfactant is polyoxyethylene sorbitan monolaurate. Other useful surfactants are known to those skilled in the art.

Each part of the liquid "TAED activator" system is kept physically separated (through packaging). Both parts are then added to the formulated hydrogen peroxide solution, and peracetic acid is generated. The concentration of peracetic acid generated depends on the quantities of activator and hydrogen peroxide selected. Again, this product, upon activation, will have a 24-hour pot-life.

In both the first and second embodiments, the "activator" portions (dry, coated TAED in the first embodiment or two-part liquid TAED/alkaline solution in the second embodiment) are mixed with a specifically-formulated liquid hydrogen peroxide solution, which contains a surfactant to aid both in wetting of the product in use and controlling the foam profile on activation. Useful surfactants for the hydrogen peroxide solution can be anionic, nonionic or amphoteric in nature. Typical examples are sodium lauryl sulfate, sodium octyl sulfate, DOWFAX C10-L, and PLURONIC F-127. Other useful surfactants are known to those skilled in the art. Generally, non-foaming or low-foaming surfactants are preferred. The hydrogen peroxide solution may also contain a fragrance to provide a pleasing odor. The amount of hydrogen peroxide in the formulation may be as high as 10%; however, optimally it is less than about 8% but greater than 0.1%, and most preferably less than 5% but greater than 0.50%.

The pH of the hydrogen peroxide solution is about 4.5, and the pH of the inventive compositions is neutral (4-8).

Known acetyl donors useful in the inventive compositions may include aspirin (acetylsalicylic acid), n-methyl diacetamide, and triacetin; however, TAED is preferred. TAED is present in the dry activator portion of the first embodiment in amounts ranging from about 40 to about 75 weight percent, based upon the weight of the dry activator component. TAED is present in the TAED dispersion portion (activator) of the second embodiment in amounts ranging from about 30 to about 40 weight percent, based upon the weight of the TAED dispersion. Generally, one mole of TAED generates two moles of peracetic acid, but the concentration of peracetic acid generated will depend on the amounts of activator and hydrogen peroxide that are combined.

Surfactants are present in the dry activator portion of the first embodiment in amounts ranging from about 5 to about 20 weight percent, based on the weight of the dry activator portion. Surfactants are present in the TAED dispersion portion of the two-part activator of the second embodiment in amounts ranging from about 0.5 to about 5 weight percent, based upon the weight of the TAED dispersion. Surfactants are present in the alkaline solution portion of the two-part activator system in amounts ranging from about 0 to about 10 weight percent, based upon the weight of the alkaline solution. Finally, surfactants are present in the formulated hydrogen peroxide solution in amounts ranging from about 0.01 to about 2 weight percent.

Various alkalinity sources and buffers are also used in the claimed compositions. Exemplary alkalinity sources for the "dry" TAED activator portion include sodium carbonate. Glycolic acid is an example of a buffer for the TAED dispersion. These examples are not intended to be limiting. Iminodisuccinic acid derivatives are also useful as alkalinity agents in both the dry TAED activator and the two-part liquid TAED/alkaline solution activator and also function as chelating agent(s). 2-amino-2-methyl-1 propanol (AMP 95) also serves as a useful alkalinity source and solvent.

Biodegradable chelating agents are also useful as an alkalinity source and include, by way of example, tetrasodium salt of iminodisuccinic acid. Iminodisuccinic acid derivatives are preferred; however, other useful chelating agents include methylglycine diacetic acid (MGDA) and disodium ethylene diamine tetraacetic acid (EDTA).

Solvents are also used in the claimed formulations, specifically for the TAED dispersion portion of the two-part activator system. Useful exemplary solvents include PPG-2 methyl ether and AMP-95 (2-amino-2-methyl-1-propanol).

The TAED dispersion typically includes a suspending agent such as magnesium aluminum silicate or Xanthan gum; however, other suspending agents known to those skilled in the art may be used.

All embodiments may further include adjuvants such as fragrances, dyes, colors or preservatives.

Table I below shows an exemplary formulation showing ranges for the components of the first embodiment.

TABLE I

| COMPONENTS | |
|---|---|
| Raw Material | Wt. % (range) |
| Dry TAED Activator | |
| Tetraacetyleethylenediamine (TAED) | 50-85 |
| Dowfax C10L (alkyldiphenyloxide disulfonate)[1] | 10-30 |
| Baypure CX 100 (Iminodisuccinic acid, Tetrasodium salt)[2] | 1-15 |
| Sodium Carbonate[3] | 1-5 |
| Formulated Hydrogen Peroxide Solution | |
| Hydrogen Peroxide (35%) | 1-25 |
| Deionized Water | 70-98 |
| Poloxamer 407[4] | 0.01-1.0 |

TABLE I-continued

| Raw Material | Wt. % (range) |
|---|---|
| COMPONENTS | |
| Fragrance (Red Apple) | 0.01-1.0 |
| pH | 4.0-5.5 |

[1] Dowfax C10L is an anionic surfactant.
[2] Baypure CX 100 is a chelating agent and alkalinity source.
[3] Sodium carbonate is an alkalinity source
[4] Poloxamer 407 is a nonionic, PO/EO, block copolymer surfactant.

Table II below shows an exemplary formulation showing ranges for the components of the second embodiment.

TABLE II

| Raw Material | Wt. % (range) |
|---|---|
| TAED Dispersion | |
| Tetraacetyleethylenediamine (TAED) | 30.4-40.0 |
| Deionized Water | 39-69 |
| Aluminum Magnesium (Suspending Agent) | 1.0-3.0 |
| PPG-2 Methyl Ether (Solvent) | 0-10 |
| Perlastan OCV (oleolyl sarcosintate) (Anionic Surfactant) | 0.5-2.0 |
| Glycacil-L (Iodo carbamato) (Preservative) | 0-0.5 |
| Glycolic Acid (pH adjuster/buffer) | 0-2.0 |
| pH | 3.5-6.5 |
| Alkaline Solution | |
| AMP-95 (2-amino-2-methyl-1-propanol) (Alkalinity Source/Solvent) | 4.20-7.0 |
| Dowfax C10L (alkyldiphenyloxide disulfonate) | 0-7.0 |
| Baypure CX 100 (Iminodisuccinic acid, Tetrasodium salt) | 0.84-4.2 |
| Deionized Water | 81.80-94.96 |
| Ph | 11-12 |
| Formulated Hydrogen Peroxide Solution | |
| Hydrogen Peroxide (35%) | 1-25 |
| Deionized Water | 70-98 |
| Poloxamer 407 | 0.01-1.0 |
| Fragrance (Red Apple) | 0.01-1.0 |
| pH | 4.0-5.5 |

As discussed, the level concentration of peracetic acid generated varies depending on how much of the TAED activator is added to the hydrogen peroxide formulation. As stated, one mole of TAED generates two moles of peracetic acid. Generally, activator is added in quantities such that hydrogen peroxide will be in excess.

As an example, in the first embodiment, dry TAED activator may be combined with formulated hydrogen peroxide at the following ratio: 0.5-1.5 wt/wt of dry activator to 98.5-99.5% formulated hydrogen peroxide solution. This combination yields approximately 0.25% peracetic acid. As an example of the second embodiment, the TAED dispersion and alkaline solution are combined with the formulated hydrogen peroxide in the following ratio: 1-2 wt/wt TAED•dispersion; 1-2 wt/wt alkaline solution and 96-98% of formulated hydrogen peroxide solution. This combination also yields approximately 0.25% peracetic acid.

The inventive compositions have application in a wide variety of uses. The inventive compositions are useful as disinfectants/sterilants to clean floors, countertops and other high-touch areas of hospitals or other health care institutions. They are also useful to clean various hard surfaces and equipment in pharmaceutical manufacturing facilities such as counters, floors, clean rooms, laboratories and hard surfaces in animal facilities.

EXAMPLES

Example 1

Efficacy

Figure 1:
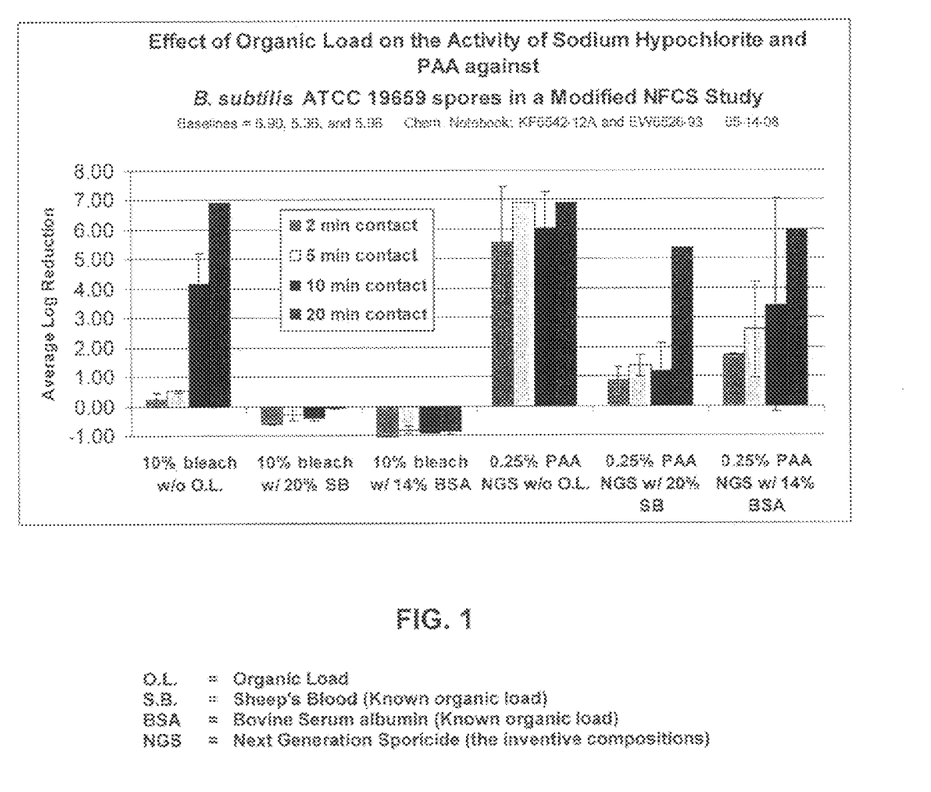
FIG. 1 is a graph which depicts superior sporicidal efficacy against *Bacillus subtilus* (in a modified Non-Food Contact Sanitizer Study) of the inventive formulation of approximately 0.25% peracetic acid as compared to a 1:10 dilution of bleach in water, in the presence of various organic loads and contact times of 2, 5, and 20 minutes.

Sporicidal efficacy of the two-part liquid activator/formulated hydrogen peroxide system in a modified Non-Food Contact Sanitizer (NFCS) study is shown in FIG. 1. The results show that the inventive formulation, which generated approximately 0.25% peracetic acid, was superior to bleach (1:10 dilution in water) against *Bacillus subtilus*, a known spore former, in the presence of various organic loads and varying contact times. *Bacillus subtilus*, ATCC 19659 is useful as a surrogate for spore forming bacteria, such as anthrax, among others.

Example 2

Efficacy

Sporicidal efficacy of the inventive compositions was tested, using the Quantitative Carrier Test 2 (QCT-2) method against *C.diff* spores. The inventive composition shown in Table III was tested at various concentrations and mixed as indicated below.

TABLE III

| Ingredient | Function | Amount (wt. %) |
|---|---|---|
| Dry TAED Activator | | |
| Tetraacetylethylenediamine (TAED) | Active Ingredient | 63.58% |
| Alkyldiphenyl Oxide Disulfonate (Dowfax C10L - 45% active (aq)) | Anionic Surfactant/ Dispersant | 11.49% |
| Tetrasodium Iminodisuccinate | Chelating Agent/ Alkalinity Source | 22.26% |
| Sodium Carbonate | Alkalinity Source/ Buffer | 2.67% |

| Ingredient | Function | Concentration |
|---|---|---|
| Formulated Liquid Hydrogen Peroxide | | |
| 35% Hydrogen Peroxide (aq) | Active Ingredient | 2.86% |
| Deionized Water | — | 96.79% |
| Poloxamer 407 | Nonionic Surfactant | 0.05% |
| Fragrance | Fragrance | 0.30% |

Dilutions:
To generate 0.050% peracetic acid, 0.225 grams of the dry TAED activator was added to 200 mL of the formulated hydrogen peroxide.
To generate 0.075% peracetic acid, 0.337 grams of the dry TAED activator was added to 200 mL of the formulated hydrogen peroxide.
To generate 0.100% peracetic acid, 0.449 grams of the dry TAED activator was added to 200 mL of the formulated hydrogen peroxide.
To generate 0.125% peracetic acid, 0.562 grams of the dry TAED activator was added to 200 mL of the formulated hydrogen peroxide.
To generate 0.150% peracetic acid, 0.674 grams of the dry TAED activator was added to 200 mL of the formulated hydrogen peroxide.
To generate 0.175% peracetic acid, 0.786 grams of the dry TAED activator was added to 200 mL of the formulated hydrogen peroxide.

To generate 0.200% peracetic acid, 0.898 grams of the dry TAED activator was added to 200 mL of the formulated hydrogen peroxide.

To generate 0.250% peracetic acid, 1.123 grams of the dry TAED activator was added to 200 mL of the formulated hydrogen peroxide.

Figure 2:
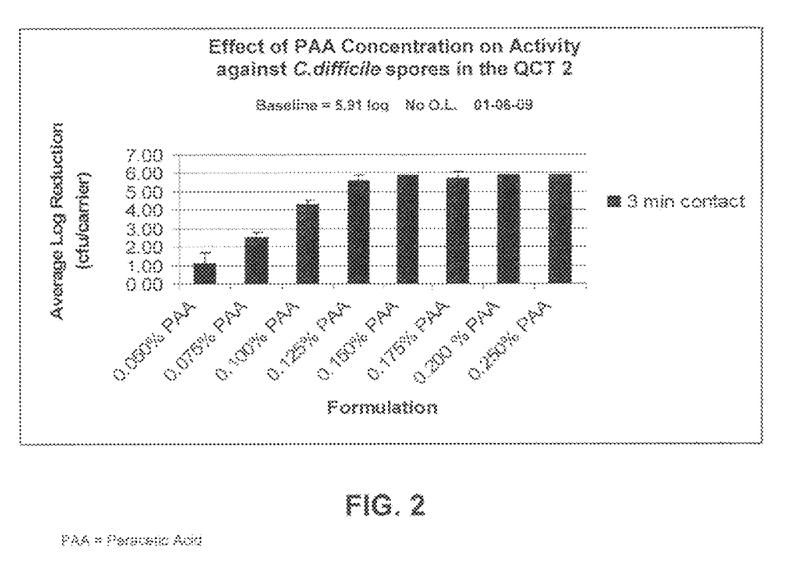
FIG. 2 is a bar graph which shows the effect of varying concentrations of peracetic acid (PAA) against *C. difficile* spores in a Quantitative Carrier Test 2 (QCT-2) for a three minute contact time.

PAA generated from the powdered activator/formulated liquid hydrogen peroxide system, at various use concentrations, is shown in FIG. 2. FIG. 2 shows average log reduction (cfu/carrier) for varying concentrations of PAA for a 3 minute contact time. Results reflect excellent activity against *C. diff* spores for peracetic acid levels of greater than 0.075% at 3 minute contact time. Efficacy was demonstrated by a log reduction of greater than 5.

Example 3

Effect of Soil Load

The effect of organic soil load on average log reduction using QCT-2 testing was also evaluated. The formulation used is set forth in Table IV below.

TABLE IV

| Dry TAED Activator | | |
| --- | --- | --- |
| Ingredient | Function | Amount |
| Tetraacetylethylenediamine (TAED) | Active Ingredient | 0.2757 grams |
| Alkyldiphenyl Oxide Disulfonate (Dowfax C10L - 45% active (aq)) | Anionic Surfactant/ Dispersant | 0.0498 grams |
| Tetrasodium Iminodisuccinate | Chelating Agent/ Alkalinity Source | 0.1107 grams |
| Sodium Carbonate | Alkalinity Source/Buffer | 0.0133 grams |
| Polyvinyl Alcohol Film* | Film Material | 0.0792 grams |
| Formulated Liquid Hydrogen Peroxide | | |
| Ingredient | Function | Concentration (wt. %) |
| 35% Hydrogen Peroxide (aq) | Active Ingredient | 2.86% |
| Deionized Water | — | 96.79% |
| Poloxamer 407 | Nonionic Surfactant | 0.05% |
| Fragrance | Fragrance | 0.30% |

*PVA film was added to have the powder in a PVA water-soluble pouch that dissolves upon "activation." Studies have shown it had no impact on efficacy or peracetic acid generation. The above powder composition was added to 200 mL of the formulated hydrogen peroxide to form a solution containing about 0.075% PAA solution (~6% TAED).

Figure 3:
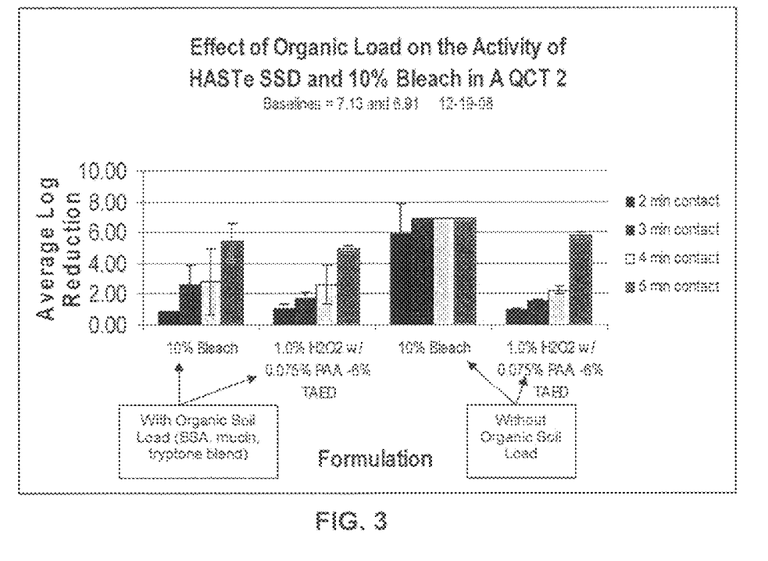
FIG. 3 is a bar graph which shows the effect of soil load on the inventive formulations versus a 10% bleach solution against *C. difficile* spores.

Sporicidal efficacy of the powdered activator/formulated liquid hydrogen peroxide system against *C. diff* spores was not affected by the presence of soil load. As seen in FIG. 3, sporicidal efficacy of a 10% bleach solution against *C.diff* spores was greatly affected, whereas the effect of soil load on the inventive formulations was minimal.

In accordance with the patent statutes, the best mode and preferred embodiment have been set forth; the scope of the invention is not limited thereto, but rather by the scope of the attached claims.

What is claimed is:

1. A two-part system for generating, in situ, a low-odor, neutral aqueous solution of peracetic acid for use as a hard surface disinfectant having sporicidal capabilities, consisting essentially of:
   a. in a first part, a dry activator solids blend consisting of: (i) a solid acetyl donor, consisting of tetraacetylethylenediamine (TAED) pre-coated with a surfactant, (ii) combined with at least two solid alkalinity sources, wherein the acetyl donor is present in amounts ranging from about 40 to about 75 wt. %, based upon the total weight of the blend; and
   b. in a second part, a hydrogen peroxide solution consisting of hydrogen peroxide, an anionic, non-ionic or amphoteric surfactant, or mixtures thereof, a fragrance and water, wherein hydrogen peroxide is present in amounts less than about 10 wt. %,
   wherein the first and second parts are mixed together just prior to use to form the peracetic acid solution having low levels of detectable hydrogen peroxide remaining in solution, and
   wherein the amount of peracetic acid formed is at least about 0.075%.

2. The two-part system as set forth in claim 1, wherein the alkalinity sources of the dry solids blend consist of sodium carbonate and the tetrasodium salt of iminodisuccinic acid.

3. The two-part system as set forth in claim 1, wherein the surfactant used to pre-coat the TAED is an anionic surfactant consisting of alkyl diphenyl oxide disulfonate, n-oleoyl sarcosinate or dodecyl benzene sulfonic acid.

4. The two-part system as set forth in claim 1, further consisting essentially of a chelating agent or a buffer, or mixtures thereof.

5. The two-part system as set forth in claim 1, wherein the hydrogen peroxide solution consists of less than about 3 wt. % hydrogen peroxide.

6. The two part system as set forth in claim 1, wherein the hydrogen peroxide solution consists of less than about 1.5 wt. % hydrogen peroxide.

7. A two-part system for generating, in situ, a low-odor, neutral aqueous solution of peracetic acid for use as a hard surface disinfectant having sporicidal capabilities consisting of:
   a. as a first part, a liquid activator system consisting of an acetyl donor and an alkalinity source, both dispersed in a water, a solvent, or mixtures thereof; a suspending agent; a buffer; a surfactant and a preservative, wherein the acetyl donor is present in amounts ranging from about 30 to about 40 wt. %, based upon the total weight of the dispersion; and
   b. as a second part, a hydrogen peroxide solution consisting of hydrogen peroxide, an anionic, non-ionic or amphoteric surfactant, or mixtures thereof, a fragrance and water, wherein the hydrogen peroxide is present in amounts less than about 10 wt. %,
   wherein the liquid activator system and hydrogen peroxide solution are mixed just prior to use to form peracetic acid solution having low levels of detectable hydrogen peroxide remaining in solution, and
   wherein the amount of peracetic acid formed is greater than about 0.075%.

8. The two-part system as set forth in claim 7, wherein the suspending agent is magnesium aluminum silicate or Xanthan gum.

9. The two-part system as set forth in claim 7, wherein the alkalinity source comprises a hydroxide, an amine or a chelating agent, or combinations thereof.

10. The two-part system as set forth in claim 7, wherein the alkalinity source comprises sodium hydroxide, monoethanolamine, or 2-amino-2-methyl-1 propanol, or combinations thereof.

11. The two-part system as set forth in claim 7, wherein the surfactant is an anionic or nonionic surfactant, or combinations thereof.

12. The two-part system as set forth in claim 11, wherein the anionic surfactant is n-oleoyl sarcosinate, alkyldiphenyl oxide disulfonate, or dodecylbenzene sulfonic acid, or combinations thereof.

13. The two-part system as set forth in claim 11, wherein the nonionic surfactant is polyoxyethylene sorbitan monolaurate.

14. The two-part system as set forth in claim 7, wherein the solvent is polypropylene glycol methyl ether.

15. The two-part system as set forth in claim 7, wherein the buffer is glycolic acid.

16. A two-part system for generating, in situ, a low-odor, neutral aqueous solution of peracetic acid for use as a hard surface disinfectant having sporicidal capabilities consisting of:
   a. tetraacetylethylene diamine (TAED) in dry form, pre-coated with a surfactant that is alkyldiphenyloxide disulfonate;
   b. two solid alkalinity sources consisting of tetrasodium iminodisuccinate and sodium carbonate; and
   c. a hydrogen peroxide solution consisting of hydrogen peroxide in amounts less than about 3 wt. %, a poloxamer surfactant, a fragrance and water.

* * * * *